US012607619B2

(12) United States Patent
Mazza et al.

(10) Patent No.: US 12,607,619 B2
(45) Date of Patent: Apr. 21, 2026

(54) ASPIRATION DEVICE FOR DETERMINING MECHANICAL PROPERTIES OF SOFT TISSUES AND METHODS THEREFOR

(71) Applicant: ETH Zurich, Zurich (CH)

(72) Inventors: Edoardo Mazza, Wettingen (CH); Bettina Thumm, Wallisellen (CH)

(73) Assignee: ETH Zurich, Zurich (CH)

( * ) Notice: Subject to any disclaimer, the term of this patent is extended or adjusted under 35 U.S.C. 154(b) by 372 days.

(21) Appl. No.: 18/286,972

(22) PCT Filed: Mar. 29, 2022

(86) PCT No.: PCT/EP2022/058210
§ 371 (c)(1),
(2) Date: Oct. 13, 2023

(87) PCT Pub. No.: WO2022/218684
PCT Pub. Date: Oct. 20, 2022

(65) Prior Publication Data
US 2024/0201163 A1 Jun. 20, 2024

(30) Foreign Application Priority Data
Apr. 14, 2021 (EP) .................................... 21168336

(51) Int. Cl.
*G01N 33/483* (2006.01)
*A61B 5/00* (2006.01)
(Continued)

(52) U.S. Cl.
CPC ......... *G01N 33/4833* (2013.01); *A61B 5/442* (2013.01); *A61B 2562/0247* (2013.01)

(58) Field of Classification Search
CPC ................ G01N 33/4833; A61B 5/442; A61B 2562/0247; A61B 5/6834; A61B 5/0055;
(Continued)

(56) References Cited

U.S. PATENT DOCUMENTS

| 2011/0130683 A1* | 6/2011 | Sarvazyan ............. A61B 5/441 |
| | | 600/587 |
| 2012/0209146 A1* | 8/2012 | Matsumoto .............. G01N 3/12 |
| | | 600/587 |
| 2019/0254587 A1 | 8/2019 | Mazza et al. |

OTHER PUBLICATIONS

Müller Bettina et al., "A novel ultra-light suction device for mechanical characterization of skin", PLOS ONE, Aug. 9, 2018, 22pages.
(Continued)

*Primary Examiner* — Brandi N Hopkins
(74) *Attorney, Agent, or Firm* — Sughrue Mion, PLLC

(57) ABSTRACT

An aspiration device (110) for measuring the viscoelastic deformability of biological tissues and synthetic materials comprises a probe head (11), a probe channel (41), a pressure unit (20), a pressure sensor (31) and a control unit (60). The first probe channel (41) is connecting the pressure unit (20) providing a vacuum with the probe head and includes the pressure sensor (31) detecting the pressure in the first probe channel (41). The first probe channel (41) has a distal end (141) leading with its lower open end (144) through the top wall (14) into the cavity (15) of the probe head. The cavity (15) comprises either an opening (16) in the side or top wall (13, 14) or a second probe channel connected with a valve. A measurement cycle comprises applying under pressure in the first probe channel (41), measuring the under pressure with the pressure sensor (31), detecting a change of under pressure increase over time (301, 401), increasing the under pressure to a predetermined maximum under pressure (303), decreasing the under pressure beyond this point in time and detecting a change of under pressure decrease over time (302, 402).

15 Claims, 12 Drawing Sheets

(51) Int. Cl.
*G01N 3/10* (2006.01)
*G01N 33/44* (2006.01)

(58) Field of Classification Search
CPC ....... A61B 5/0053; A61B 8/54; A61B 5/6852;
A61B 6/032; A61B 1/00094; A61B
17/22012; A61B 1/00073; A61B 5/4337;
A61B 17/22; A61B 5/441; A61B
17/320016; A61B 5/435; A61M 1/916;
A61M 1/008; A61M 1/0084; A61M
5/484; A61M 5/178; A61C 19/04; G01L
13/02
See application file for complete search history.

(56) References Cited

OTHER PUBLICATIONS

International Search Report for PCT/EP2022/058210 dated Jun. 8,
2022 [PCT/ISA/210].
Written Opinion for PCT/EP2022/058210 dated Jun. 8, 2022 [PCT/
ISA/237].

* cited by examiner p1 ..........

curve fit ——

300

400

506

501

502

503

504

505

61

504

505

405

604"

Loading phase

Unloading phase (Skin Tension)

Unloading phase (Skin Suction)

ASPIRATION DEVICE FOR DETERMINING MECHANICAL PROPERTIES OF SOFT TISSUES AND METHODS THEREFOR

TECHNICAL FIELD

The present invention relates to an aspiration device for determining mechanical properties of soft tissues, especially biological tissues and synthetic materials, and methods therefor.

PRIOR ART

EP 3 318 181 A1 discloses an aspiration device for measuring the viscoelastic deformability of biological tissues and synthetic materials, comprising a probe head having the form of a cup with a cavity, side walls and a top wall, a first probe channel, a pressure unit and a control unit, the first probe channel being configured to connect the pressure unit, that provides a vacuum inside the first probe channel and that is controlled by the control unit, with the probe head. The first probe channel has a distal end leading through the top wall into the cavity, optionally extending at least partly into the cavity. An aspiration device with these features is also known from EP 3 141 180.

EP 3 318 181 A1 further comprises a second probe channel having a distal end leading through the top wall into the cavity and being connected with a pressure sensor provided to determine the pressure in the cavity and to communicate it to the control unit to determine the point in time, when deformed tissue or material closes the distal end of the first probe channel based on a pressure difference in the two probe channels.

EP 3 141 180 has in addition a plug displaceable arranged within the cavity and a pressure sensor to determine the pressure in the cavity and to communicate it to the control unit, wherein the control unit is configured to determine the deformation of the soft tissue using the pressure value when the plug covers and closes the distal end defining a final position when the housing is attached to the soft tissue.

US 2011/130683 A1 discloses a method for assessing viscoelastic properties of soft tissues based on detecting an inflection point on a pressure-time plot when air is aspirated from a cavity placed over the tissue sample. A small diameter tube through which air aspiration is conducted is ultimately closed off by tissue being drawn into the cavity causing an abrupt change in pressure slope. First or second derivatives of the pressure-time plot can be used to detect the inflection point. It is stated that repeating the test with different aspiration rates or after a predetermined relaxation time allows determining tissue viscosity and tissue creep in addition to tissue stiffness expressed as Young's modulus.

EP 0 255 809 discloses a device for the measurement of the elasticity of the human skin, by which a negative pressure is created in an area of the skin up to reaching a predetermined value and the temporary deformation of the skin itself is measured; by returning the negative pressure to the zero value, the deformation of the skin in correspondence with that value is measured, i.e., the permanent deformation of the skin.

SUMMARY OF THE INVENTION

The possibilities of these devices are aimed towards obtaining information and data about the viscoelastic behaviour of the soft tissue under investigation. Based on this prior art it is an object of the present invention to provide an aspiration device capable to provide data relating further mechanical properties of the soft tissue under investigation. Said soft tissue can be of biological nature or a synthetic material.

The principle of the aspiration device according to the invention is based on features related to the suction method, where the soft tissue, which can be biological tissue or synthetic material, is drawn into a defined cavity with a negative pressure. Therefore, the tissue is deformed due to application of a certain load. With the information of the tissue deformation and the applied load, several mechanical properties of the investigated tissue can be determined.

Relating to the tissue in question, there are a number of materials which can be tested in vivo or ex vivo.

As in vivo tissue: skin and mucous membranes of humans or animals. Skin is the natural outer layer that covers a person, animal or fruits. Mucous membranes comprise directly reachable surfaces inside the mouth, nose, vagina, cervix. Skin can be covered by hair or fur or is not covered by hair or fur.

The following materials can be tested as ex-vivo and in-vitro tissue: compliant elastomers or other synthetic materials, hydrogels, tissue engineering scaffolds, decellularized extracellular matrix, cellulose based materials, organotypic in-vitro systems, or soft implants. Soft implants are e.g., breast implant bodies or other flexible surfaces, also comprising meshes with closed mainly impermeable surfaces which are to be tested ex-vivo.

The tissue material also comprises artificial skin or skin substitutes. These materials can be tested ex-vivo as such and also in-vivo after transplantation, since these materials form then part of the skin of the mammal in question.

An aspiration device for measuring the viscoelastic behaviour of biological tissues and synthetic materials, comprises a probe head having the form of a cup with a cavity, side wall(s) and a top wall, a first probe channel, a pressure unit, a pressure sensor and a control unit, the first probe channel connecting the pressure unit, that provides a vacuum inside the first probe channel and that is controlled by the control unit, with the probe head and including the pressure sensor detecting the pressure in the first probe channel and connected with the control unit. The first probe channel has a distal end leading with its lower open end through the top wall into the cavity of the probe head, wherein optionally the lower open end is extending into the cavity. The cavity comprises either an opening in the side or top wall, or a second probe channel connected with a valve, connected with the control unit and the valve connecting the second probe channel with the environment. In both cases the control unit is configured to execute a measurement cycle comprising the applied underpressure in the first probe channel, measuring the underpressure with the pressure sensor, detecting a change of underpressure increase over time, increasing the underpressure to a predetermined maximum underpressure, decreasing the underpressure beyond this point in time and detecting a change of underpressure decrease over time.

The pressure value $p_{close}$ and time value $t_{close}$ at the change of underpressure increase over time as well as the pressure value $p_{open}$ and time value $t_{open}$ at the change of underpressure decrease over time are determined and/or transmitted to the control unit. The first pressure/time value pair is related to the closing of the lower end of the first probe channel, when the tissue completely obstructs this opening, effectively separating the volume of the probe cavity from the first probe channel. The second pressure/time value pair is related to the re-opening of the lower end of the first probe channel, when the tissue no longer completely obstructs this opening, effectively bringing the volume of the probe cavity and of the first probe channel again together.

When the aspiration device comprises the second probe channel connected with said valve, then the measurement cycle can be executed by the control unit while the valve is open over the measurement cycle. This measurement cycle is almost identical with the aspiration device having a probe head with an opening in the side wall.

On the other side, an amended measurement cycle can be conducted, when the second probe channel connected with said valve is present, i.e., the measurement cycle can be executed by the control unit while the valve is closed over the measurement cycle. The above mentioned first and second pressure/time value pairs are then different.

A filter can be provided in one or more of the probe channels for cleaning the air sucked in to avoid particles from the tissue surface under monitoring.

The opening pressure value ($p_{open}$) and/or the opening time value ($t_{open}$) can be determined based on the detection of a constant under pressure time during the under pressure decrease when the cavity is closed beside the first probe channel or comprises a closed valve, when the biological tissue or synthetic material re-opens the first probe channel during under pressure decrease. These values can be detected when the pressure curves meet again, or when the slopes change: $p_2$ shows this under pressure plateau and $p_1$ shows a drop to be detected. The reading of $p_{open}$ can be determined with the help of the pressure output in $p_1$. But it would also be conceivable to determine $p_{open}$ by the drop in the $p_2$ curve, or by the coincidence of $p_1$ and $p_2$.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
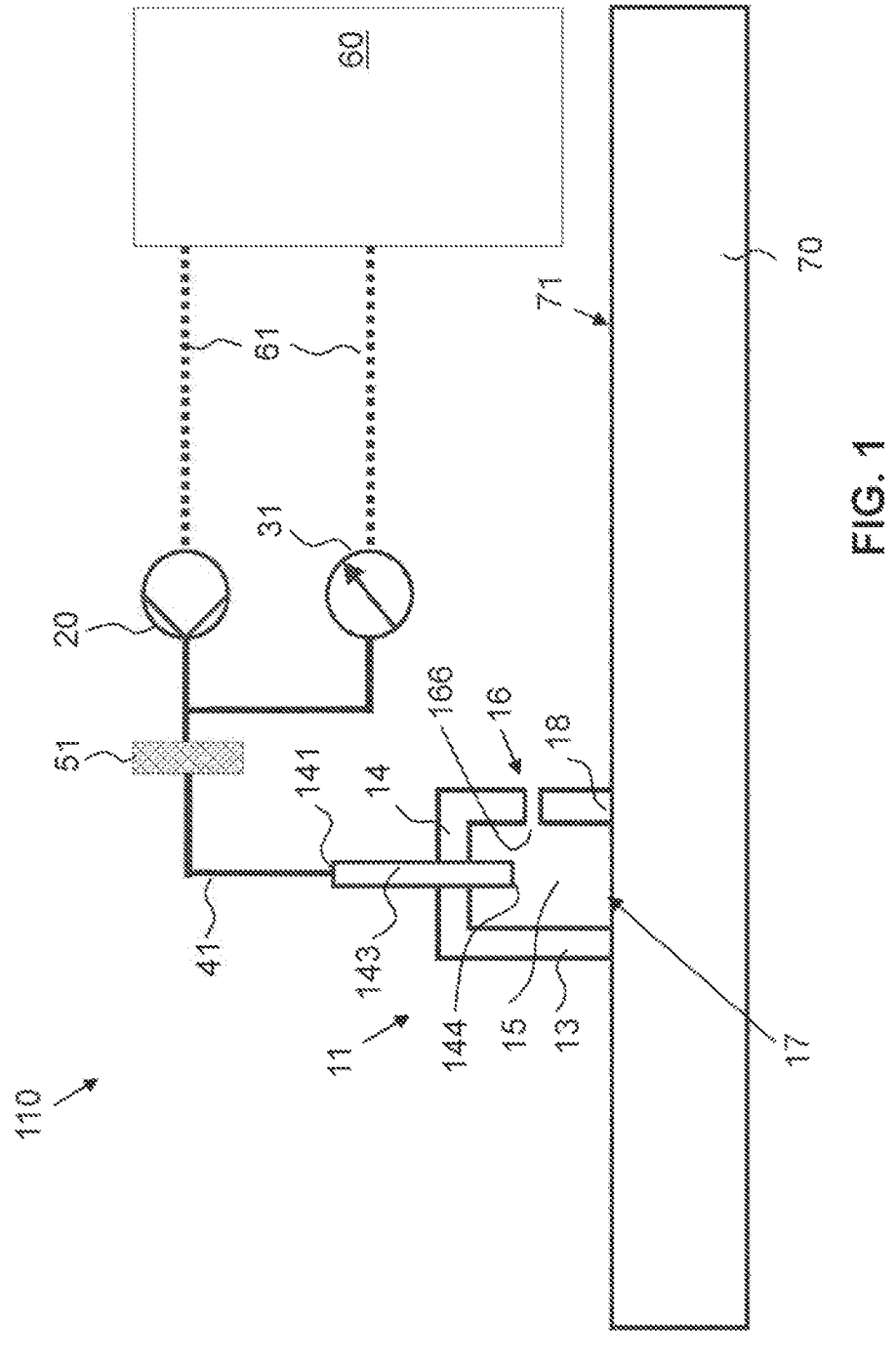
FIG. 1 shows a schematic representation of an aspiration device according to a first embodiment of the invention, called the tissue tension scheme.

FIG. 1 shows a schematic representation of an aspiration device 110 according to a first embodiment of the invention relating to a tissue tension protocol. It comprises an aspiration probe 11 with one air channel 41 connected to a pressure sensor 31. The one air channel, also first air channel 41 in comparison to the second air channel 42 present in a later explained second embodiment aspiration device 310, can be a tube, especially a flexible tube, but stiff enough not to change its inner volume while in under pressure.

The aspiration probe 11 comprises side walls 13 and a top wall 14 spanning up an internal cavity 15 which has an open bottom mouth 17. The side walls 13 and top wall 14 can span up a cube as a cavity 15, but the aspiration probe 11 can also have the shape of a hollow cylinder as e.g., shown in EP 3 141 180 with a round bottom edge 18.

The main feature of the aspiration probe is the open bottom mouth 17 with a flat surface directed to the tissue to be tested. The volume as such can be determined in different ways, beside the cylindrical side walls (in a view from above) polygonal or elliptical side walls are possible.

The tube or first air channel 41 can comprise an adapter 141 with which a rigid hollow tube end portion 143 can be positioned in a predetermined distance from the top wall 14 and at the same time the lower tube open end 144 at a specific vertical distance from the bottom edge 18. It is possible that the position of the rigid hollow tube end portion 143 is adjustable, slightly influencing the volume of the probe cavity 15.

A pressure unit 20 is connected to the vertical air channel 41 and establishes the negative pressure, which is needed to draw the soft tissue/biological tissue 70 into the probe cavity 15. A small opening 16 in the aspiration probe side wall 13 serves to equalize the pressure inside the chamber or cavity 15 of the aspiration probe 11 with atmospheric pressure during the second phase of the measurement as will be explained below. The inner opening position 166 of the small opening 16 in the side wall 13 is positioned lower than the lower open end 144 of the first air channel 41, but it can also be positioned higher or even beside the first air channel 41 and air channel adapter 141 in the top wall. It has not to be positioned so low that the dome-like behaviour of a sucked in tissue does obstruct the opening 16.

The aspiration probe 11 is the only part of the device in contact with the soft tissue 70 or biological tissue at the beginning of the measurement, i.e., the bottom edge 18 is in such contact. Said bottom edge 18 can have a flat surface or a rounded surface for less influence on the soft tissue 70 in contact.

An air filter 51 ensures the decoupling of the control unit with the environment, so no bacteria or any other harmful particles can be accidentally transferred from one subject to another in the case of a biological tissue measurement.

The pressure sensor 31 and the pressure unit 20 are connected via lines 61 with a control unit 60. Said lines 61 are inter alia electrical supply and data lines. The control unit 60 comprises a processor and memory for running a computer program product generating control commands for executing steps directed to the pump 20 via line 61 and accepting measurement signals via line 61 from the pressure sensor 31. The control unit 60 preferably comprises an input device like a keyboard or touch screen and an output device as a display and storage for the measured results but these elements can of course be externalized in an external or remote computer connected via a data connection to the then core control unit 60.

A specific tissue deformation profile can be achieved with the aspiration device 11 via the programmed control unit 60. To this end, air is drawn out of the aspiration probe cavity 15 through the tube 41, and a vacuum is established. The maximum vacuum level depends on the measurement protocol. Any protocol leads to a displacement-controlled soft tissue measurement, since the elevation of the tissue is limited by the position of the vertical tube 143 lower end surface 144.

Figure 2:
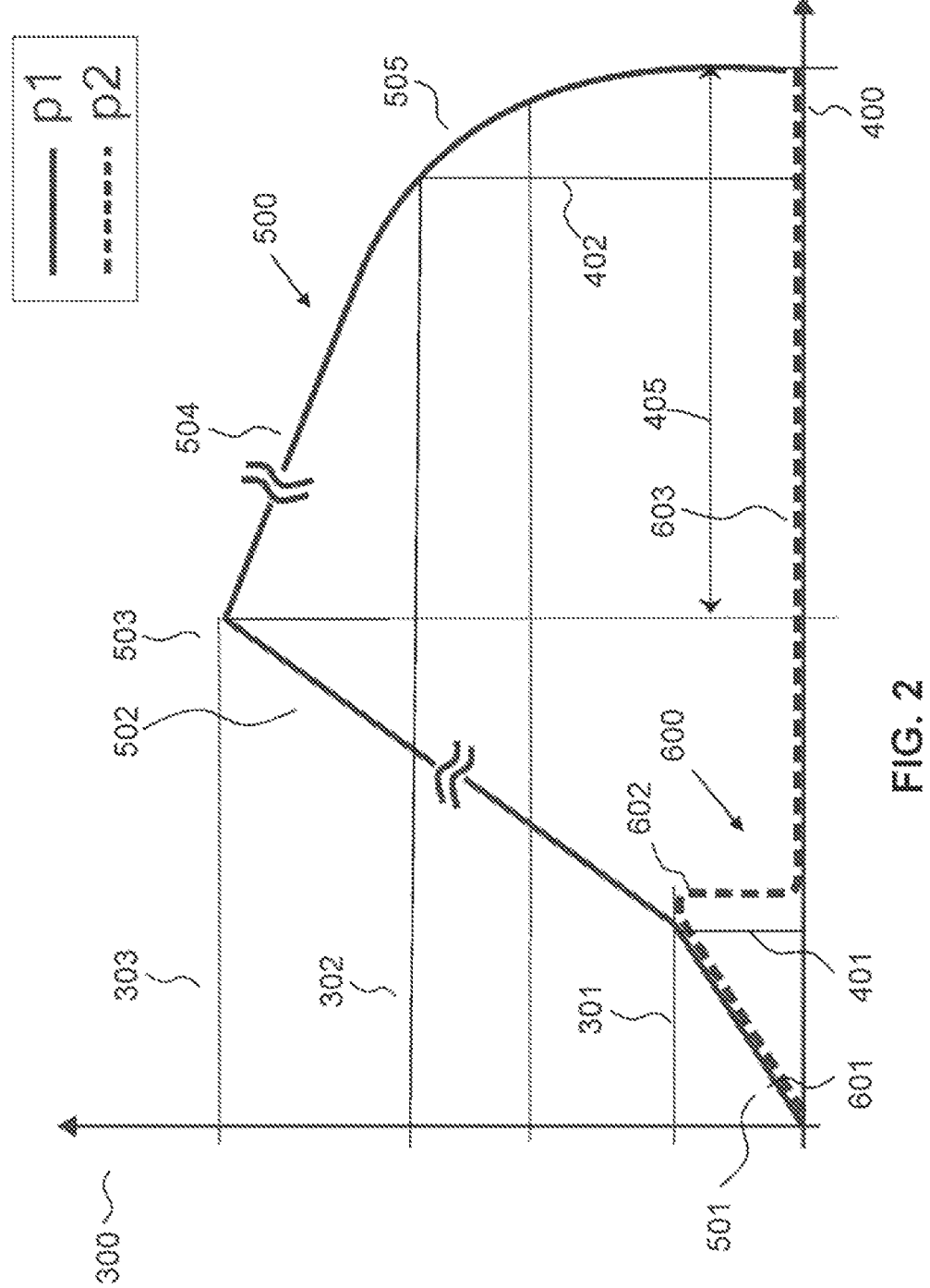
FIG. 2 shows a partially not-to-scale diagram of pressure against time during a measurement cycle of the device according to FIG. 1.

The first measurement method called tissue tension scheme, applied by the control unit 60 is a tissue tension method as shown and explained in conjunction with FIG. 2 during a measurement cycle of the device according to FIG. 1. FIG. 2 shows a partially not-to-scale diagram of negative pressure 300 against time 400. This means that the pressure value 0 means that no under pressure is present and increasing values of the pressure 300 on the y-axis is related to increasing under pressure.

Initially, within the first method, a linear pressure 501 ramp is applied on the soft tissue/biological tissue 70 and draws the tissue surface 71 in the area 17 into the aspiration probe cavity 15 until the height h which is equivalent to the position of the bottom opening 144 of the air channel is reached.

This event is detected by a change in slope of the pressure curve 500, shown as pressure curve p1 in FIG. 2. The pressure 301 at this point in time is called closing pressure $p_{close}$, i.e., the pressure which is needed to elevate the tissue 70 until closure of the lower opening of the vertical air tube 143. After reaching this elevation height h, the pressure ramp is increased and ramps up until a certain level of vacuum 303, $p_{max}$, is established in the air channel 41. In the same phase the small opening 16 in the chamber wall will enable a progressive equalization of the chamber pressure with atmospheric pressure. This is illustrated in FIG. 2 as the dotted line for pressure $p_2$ 600. This under pressure will not be measured by the device 110 and will not be taken up by the control unit 60, the illustration of $p_2$ is just for explanatory purposes. The use of a pressure sensor for $p_2$ enables further detection methods of the open and closure pressures. These methods are especially explained in conjunction with FIGS. 7 and 11.

The size of the opening 16 is such, that the pump 20 can increase the under pressure in the cavity 15, which is in this first portion following the same curve 501 or 601, although air is always rushing in. When the tissue 70 closes the lower opening 144, then the under pressure in the tube 41 increases rapidly and it is known from previous trials about the necessary time within which the under pressure increases enough to be greater than $p_{open}$, i.e., under pressure at value 302. It is also possible to increase the underpressure in a determined way to said value $p_{max}$ based on a measurement.

After reaching $p_{max}$ at pressure inversion point in time 503 the pressure unit 20 is reversed and a slow increasing pressure ramp 504 is applied in the air channel 41 such that the vacuum level decreases. In simpler embodiments, a valve can be provided in the line of tube 41 which is just opened at that point in time allowing the start of a decrease of the under pressure and no reverse of the pump 20 would be necessary. As soon as the tissue 70 detaches from the vertical air channel end 144 at elevation height h, a change in the slope of $p_1$ can be detected and an increased decrease inverse pressure 505 can be detected. This pressure 302 is called opening pressure $p_{open}$.

When the tissue 70 detaches from the vertical air channel end 144 at elevation height h, the under pressure from the tube is quickly reduced by inflowing air from the cavity 15 raising the under pressure back to the pressure of the ambient room. It has been result of experiences that this gradient depends on the detachment of the tissue. The more evenly the tissue detaches from the vertical pin, the quicker the vacuum drops, almost immediately.

Figures 3A, 3B, 3C:
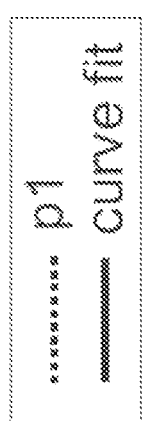
FIG. 3A shows an evaluation process for the closing pressure $p_{close}$ in the loading phase in a diagram of pressure against time during a measurement cycle of the device according to FIG. 1.
FIG. 3B shows an evaluation process for the opening pressure $p_{open}$ in the unloading phase in a diagram of pressure against time during a measurement cycle of the device according to FIG. 1.
FIG. 3C shows an evaluation process for the time parameter in the unloading phase in a diagram of pressure against time during a measurement cycle of the device according to FIG. 1, i.e., in the first embodiment of the invention.

FIGS. 3A, 3B and 3C show an evaluation process for the closing pressure $p_{close}$, the opening pressure $p_{open}$ and the time parameter of the unloading phase for the first embodiment of the invention, respectively, i.e., for the embodiment according to the aspiration device of FIG. 1.

FIG. 3A shows the evaluation of the closing pressure in the loading phase. It corresponds to the crossing point 506 of two curves, which are fitted to the slopes of the pressure curve $p_1$. FIG. 3B shows the opening pressure corresponding to the crossing point of the last two fitted curves on the pressure curve $p_1$ of the unloading phase. The fitting process starts at the pressure peak 503, where a linear curve is fitted to the increasing pressure curve. The next fitting point is where the first fitted curve deviates from the pressure curve within a predetermined threshold, and a second linear curve is fitted to the pressure curve. This process is repeated until a fitted linear curve crosses with the x-axis of the chart before the deviation is larger than the predetermined threshold of deviation. Finally, FIG. 3C shows, in addition to the pressure parameters, a time parameter characteristic 405 which can be extracted for the viscoelastic tissue behaviour: $t_{end}$–$t_{max}$ indicating the time needed for the tissue to retract fully from the vertical air channel (elevation height h).

Figure 4A:
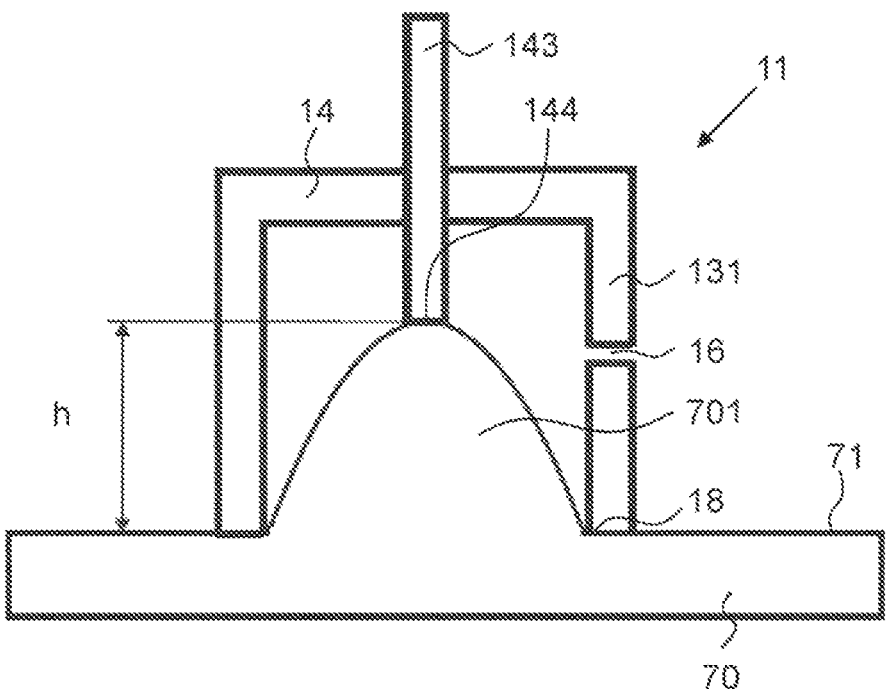
FIG. 4A shows a first deformation profile at $p_{close}$ for a tissue sucked in the aspiration device according to FIG. 1.
Figure 4B:
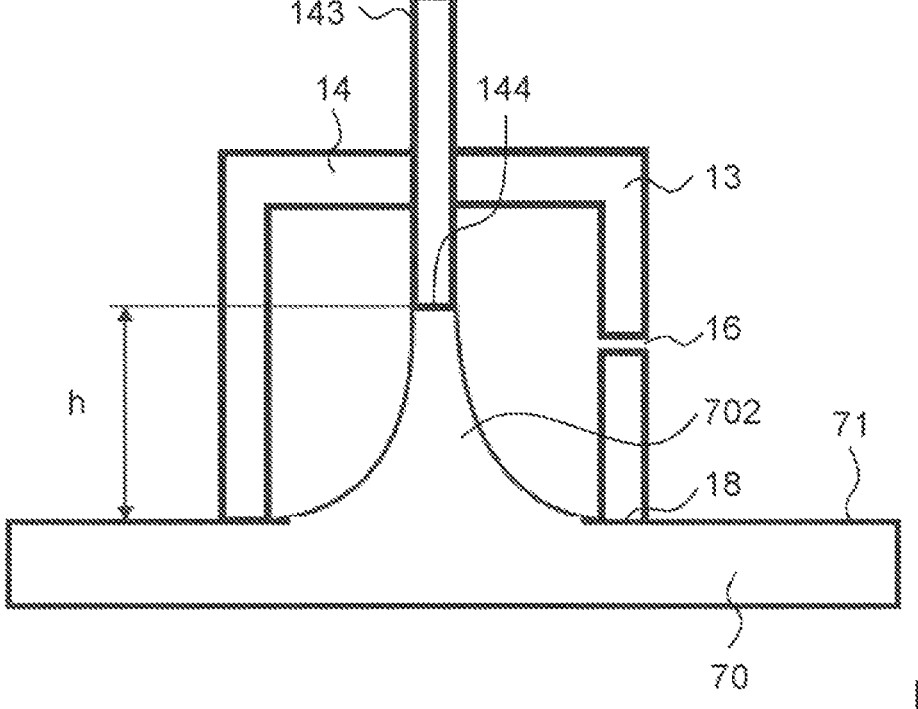
FIG. 4B shows a second deformation profile at $p_{open}$ for a tissue sucked in the aspiration device according to FIG. 1.

In this method, the tissue deformation profile is pointy. FIG. 4A shows a first deformation profile 701 at $p_{close}$ for a tissue sucked in the aspiration device according to FIG. 1 and FIG. 4B shows a second deformation profile at $p_{open}$ for a tissue sucked in the aspiration device according to FIG. 1, i.e., both within the tissue tension scheme.

FIG. 4A shows an experienced first tissue deformation profile 701 during loading, before the aspiration chamber is equalized to atmospheric pressure. The tissue 70 is held at the elevation height h, where the closing pressure is extracted ($p_{close}$). FIG. 4B shows a second tissue deformation profile 702 at the time point of detachment from the vertical air channel 143, where the opening pressure is extracted ($p_{open}$), during the unloading step. Both drawings are related to the tissue tension scheme.

The first tissue deformation profile 701 is convex and dome shaped, the second deformation profile is concave, wherein only a tissue surface equivalent to the bottom opening 144 of the tube end portion 143 stays in contact with and closes the opening. With this method it is possible to evaluate the tissue stiffness, in terms of the pressure needed to induce a certain tissue elevation (mbar/mm). This parameter depends on the specific microstructure of the tissue and is—for e.g., the biological tissue—mainly determined by the density and configuration of the collagen fibers. The closing pressure $p_{close}$ compared to the elevation height h results in the tissue stiffness $k=p_{close}/h$. Further this method enables the evaluation of viscoelastic tissue parameters, like the opening pressure ($p_{open}$) and the release ratio as defined and explained later in this specification. After reaching the maximum pressure $p_{max}$, the tissue will experience creep effects. These effects depend strongly on the microstructure, e.g., collagen fibres, the fluid flow within the tissue and the amount of proteoglycans, in case of biological tissue. The pressure at the point of retraction (when the tissue detaches from the vertical air channel bottom 144), called $p_{open}$, is characteristic for these phenomena. This is true for biological tissues being part of a human or animal, for example the skin and mucous membranes, but the effects can also be measured in artificially grown biological tissues in a technical environment, intended for later implantation. Therefore, this artificial biological material, e.g., artificial skin is biological but nevertheless the method handling is ex vivo. The tests related to the different properties are made ex vivo in the laboratory.

Figure 5:
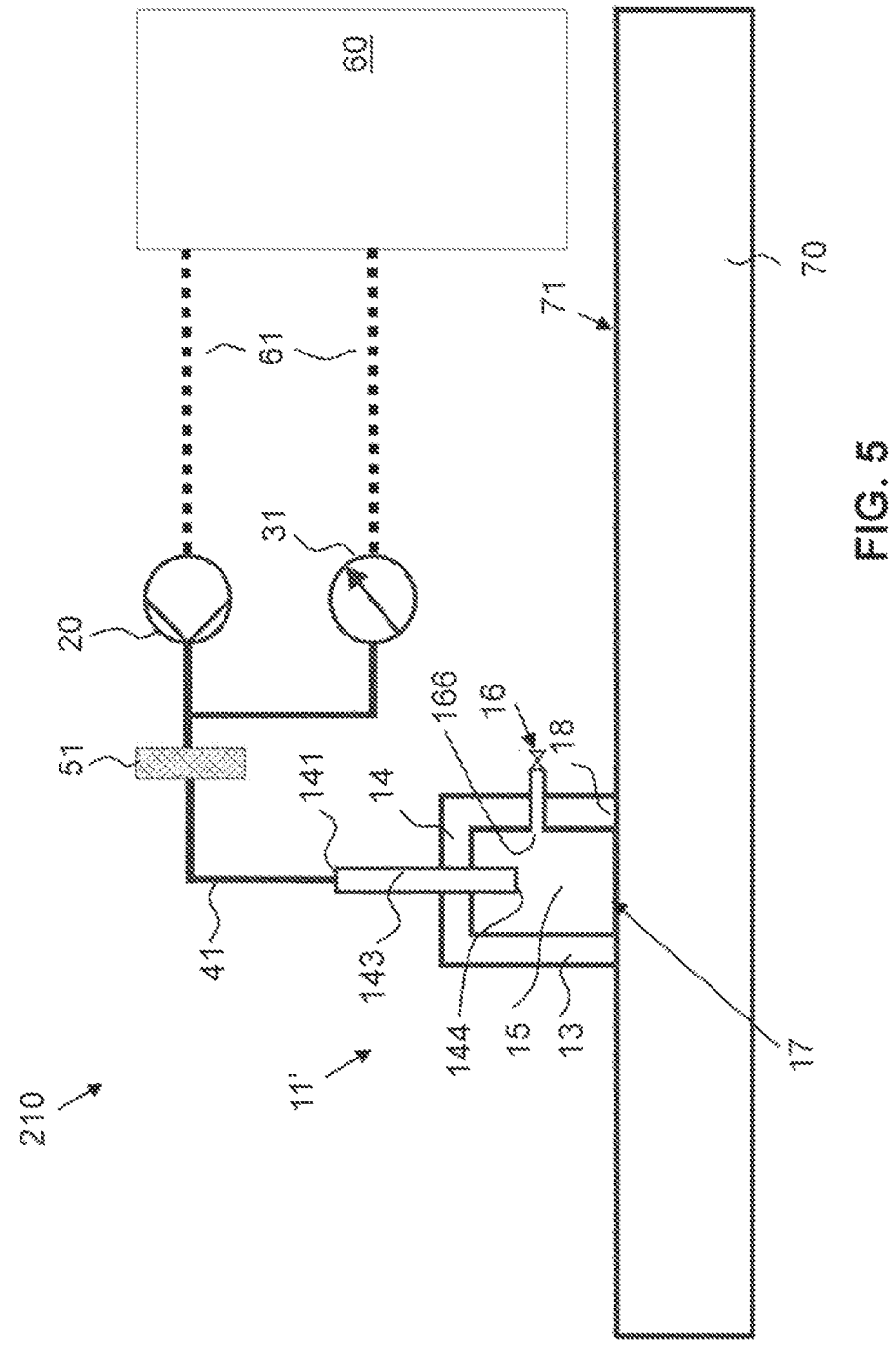
FIG. 5 shows a schematic representation of an aspiration device according to a second embodiment of the invention, called the tissue suction scheme.

FIG. 5 shows a schematic representation of an aspiration device 210 according to a second embodiment of the invention related to a tissue suction scheme. It is built essentially similar to the aspiration device 110 according to FIG. 1 with one difference, the opening 16 of FIG. 1 is closed. This can be a manual valve like indicated with the drawing symbol in FIG. 5, but it can also be an entirely closed side wall 13.

A second method called tissue suction scheme is applied with the embodiment of the aspiration device 210 as shown in FIG. 5, within which the small opening 16 in the aspiration probe wall 13 is closed, therefore no equalization of the chamber 15 pressure can take place. Besides closing the opening 16 in the device according to FIG. 5, it is also possible to use the device according to FIG. 7 while the valve 35 is closed, so the second tube 42 connected to the related elements of valve 35 is not activated.

Figure 6:
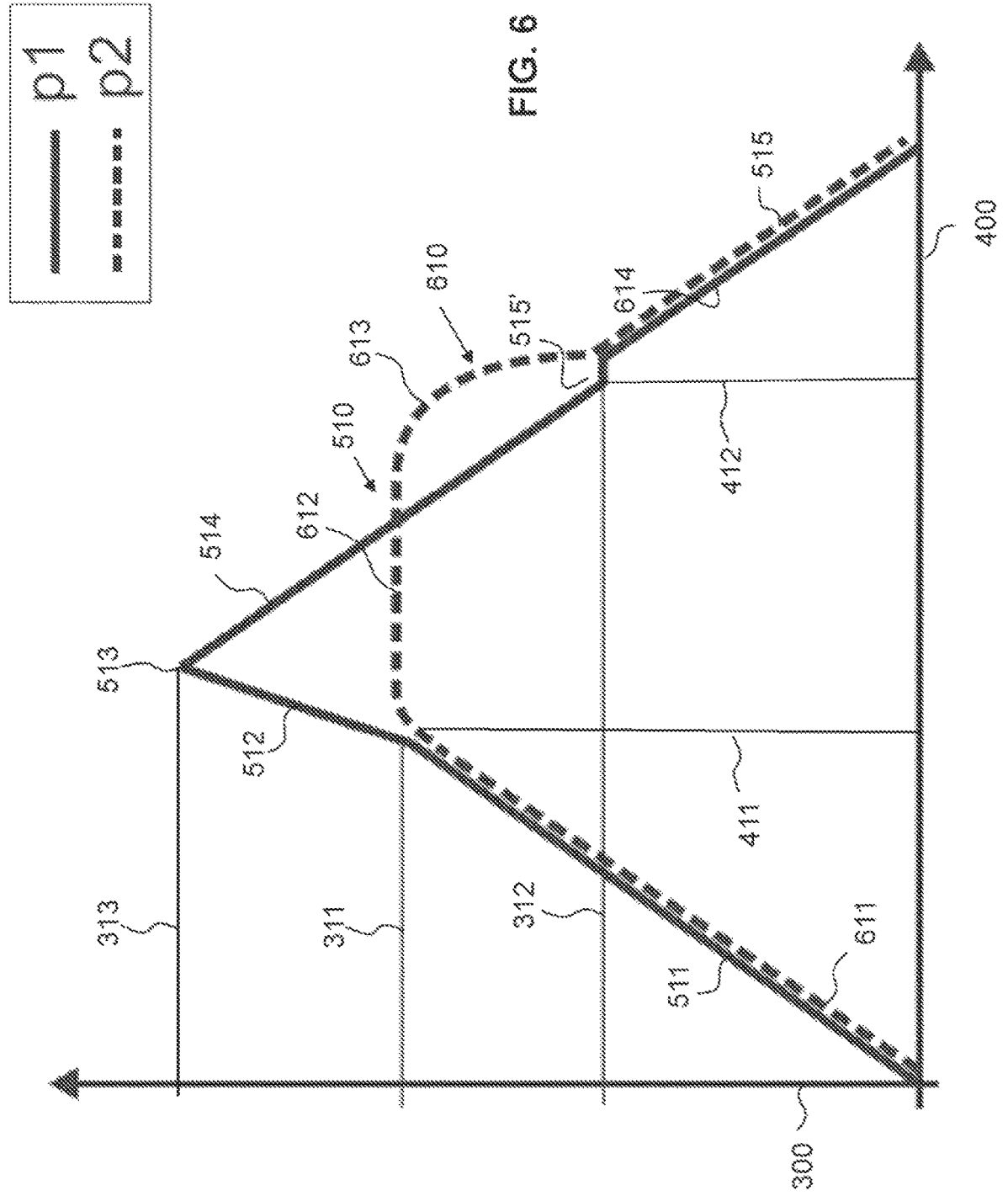
FIG. 6 shows a partially not-to-scale diagram of pressure against time during a measurement cycle of the device according to FIG. 5.

The second tissue suction method follows the pressure vs. time curve 510 of FIG. 6 and applies a linear negative pressure ramp 511 on the biological or soft tissue and draws the tissue into the aspiration probe cavity until the height h (position of the vertical air channel 144) is reached. This event is detected by a change in slope of the pressure curve similar as in the first method; here from curve portion 511 to curve portion 512. Shortly after reaching $p_{close}$, the air flow is reversed at a maximum negative pressure value 313 at point 513 and a decreasing under pressure ramp 514 is applied through reverse activation of the pump 20 or opening a valve (not shown in the drawings of FIG. 5). As a consequence, the tissue retracts and the pressure 515' at which the tissue detaches from the vertical air channel can be detected as the opening pressure $p_{open}$. In this illustration as well, $p_2$ is shown for explanatory purposes only, the chamber 15 pressure as shown in curve 610 is not measured.

Initially the two curves 511 and 611 are identical, since the bottom 144 is open and the cavity and the first tube 41 volume form a common cavity. At the negative pressure 311, $p_{close}$ at time 411, $t_{close}$, the two cavities become separated. Therefore, the curve 612 of the cavity 15 under pressure remains stable until the decreasing under pressure 514 raises above the under pressure in the cavity 15; then the under pressure 613 is decreasing too. The tissue portion at the bottom 144 is released and the two cavities 15 and 41 are reunited such that there might be a small increase of the under pressure instead of plateau 515' before the under pressure goes in unison to the environmental pressure along curves 515 and 614 with a slightly lower inclined slope due to the increased combined volume compared to the slope in curve portion 514.

Figure 7:
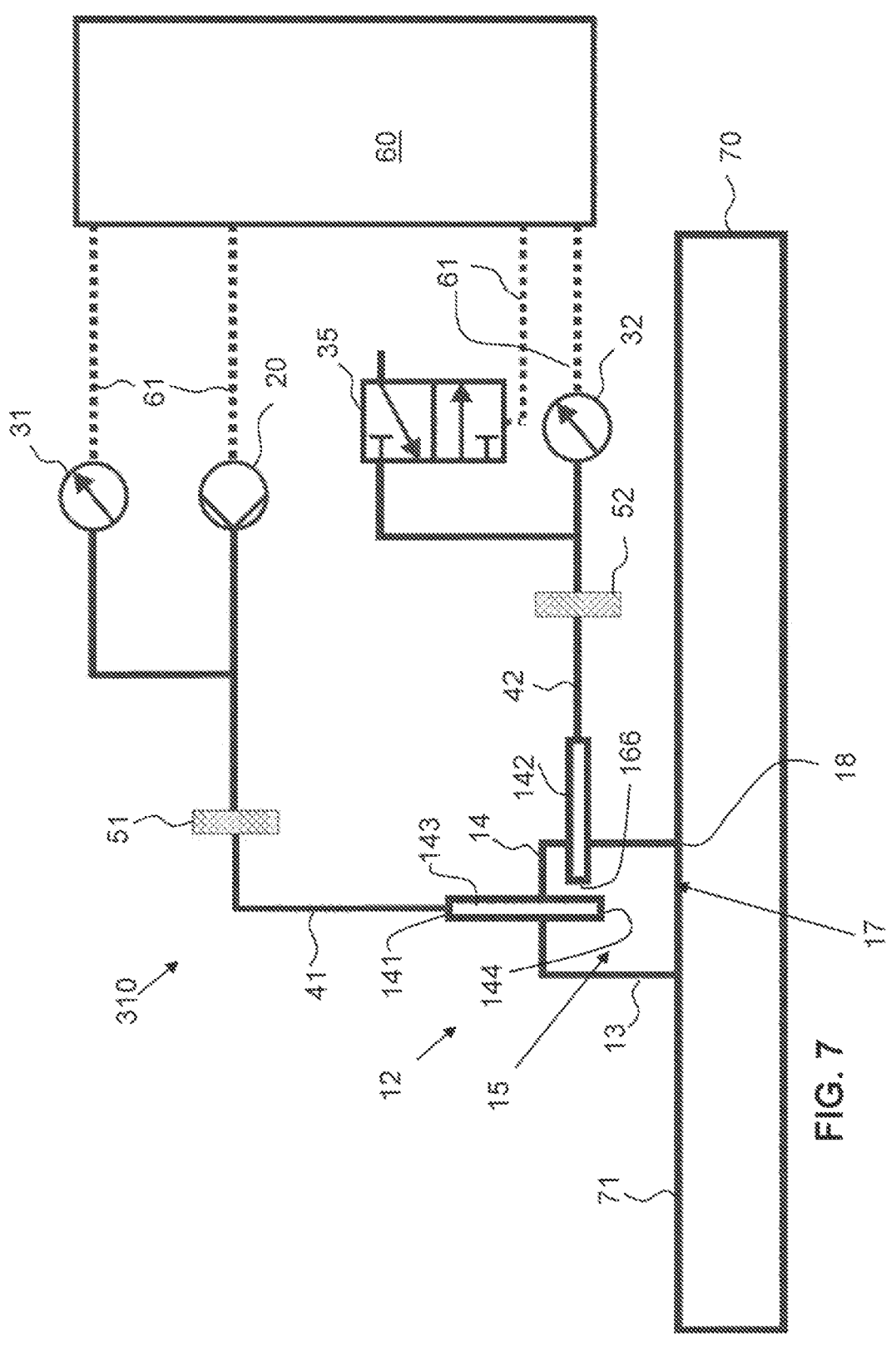
FIG. 7 shows a schematic representation of an aspiration device according to a third embodiment of the invention, called the combined device for providing the application of the tissue tension scheme and the tissue suction scheme.

FIG. 7 shows a schematic representation of an aspiration device 310 according to a third embodiment of the invention, called the combined device for providing the application of the tissue tension scheme and the tissue suction scheme beside the possibility to apply the above mentioned second method a third approach with additional elements, being a second pressure sensor 32 with a second air channel 42 and track the pressure occurring in the aspiration probe cavity 15. This would mean, that the aspiration device 310 according to this further embodiment measures the pressure $p_2$, which is indicated as dotted line in the illustrations, i.e., with a closed opening (=no opening) as shown in FIG. 6 or with such an opening 16 as in FIG. 1 as shown in FIG. 2. The opening 16 can be replaced in this case by using the opening in the probe wall 13 to apply a second air channel 42 connected to a second air filter 52, a valve 35 and the said second pressure sensor 32. This arrangement as shown in FIG. 7 is in its lay-out similar to the known aspiration device as shown in FIG. 13B of EP 3 318 181 A1. However, it has to be noted, that even though the arrangement of the device is similar to the existing one, the measurement method, meaning the way how the measurement and the evaluation of the outcome parameters is performed, is entirely different. Only the chamber pressure $p_1$ is used for the evaluation of the closing pressure $p_{close}$. Furthermore, valve 35 takes the function of opening 16 with a longer way from the cavity 15 to the environment to apply the first method explained above.

In a further slightly modified third embodiment, the suction pump 20 is provided in parallel to the pressure sensor 32, i.e., in parallel to the valve 35.

In another further slight modification of this third embodiment, the aspiration device could be used in connection with the tissue suction scheme as well, when:

channels 41 and 42 are exchanged channel 41 only comprises the pressure sensor 31 channel 42 (horizontal) comprises the elements with reference numerals 32, 35, 20. This aspiration device is similar to the aspiration device of FIG. 11 with the proviso that the pump 20 has there its own channel 43.

Figure 8:
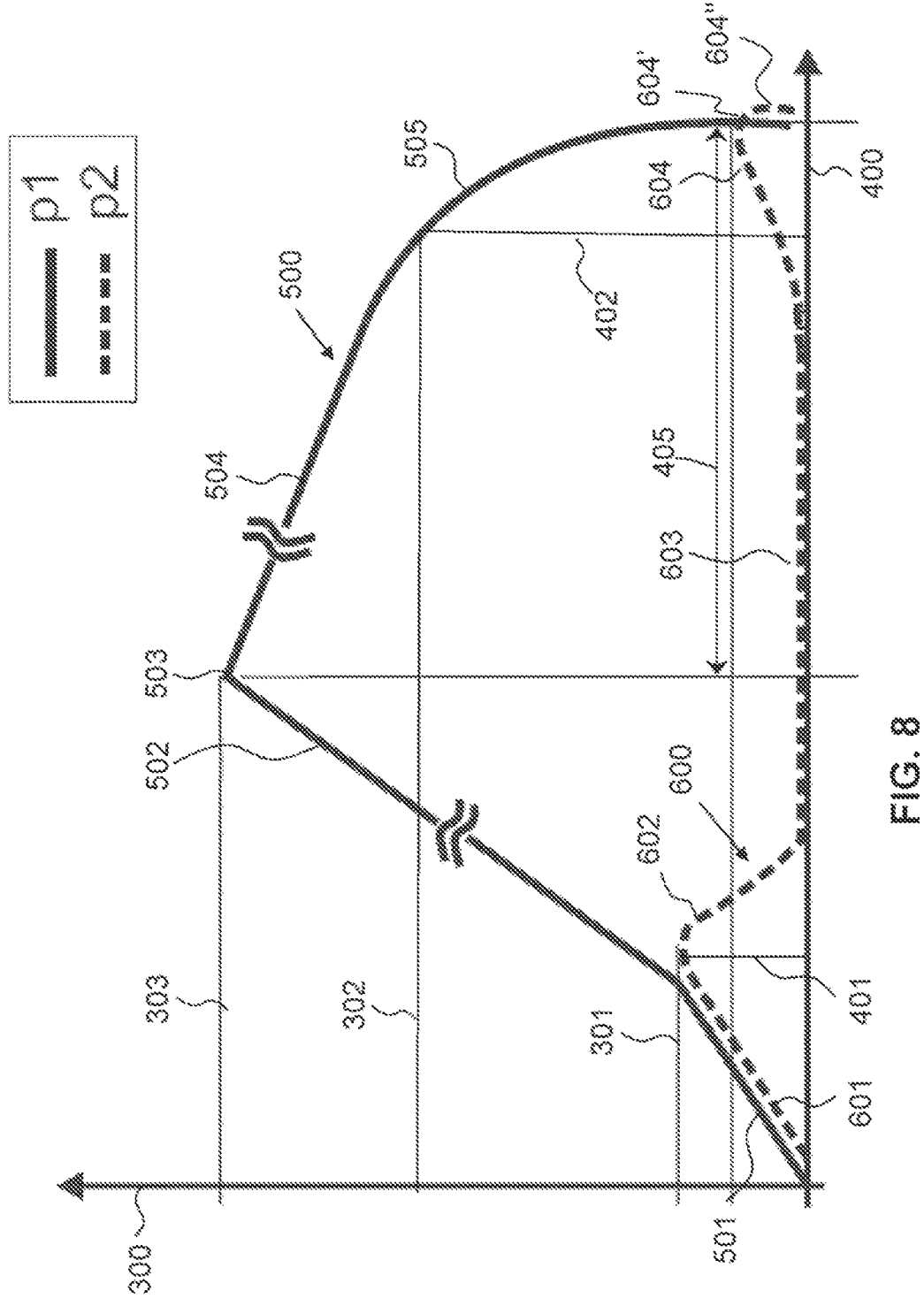
FIG. 8 shows a partially not-to-scale diagram of pressure against time during a measurement cycle of the device according to FIG. 7 for the tissue tension scheme.

The second measurement method called tissue suction scheme, applied by the control unit 60 is a tissue tension method as shown and explained in connection with FIG. 8 during a measurement cycle of the device according to FIG. 5 or when this protocol is applied, FIG. 7. FIG. 8 shows a partially not-to-scale diagram of negative pressure 300 against time 400 for the tissue suction scheme. This means that the pressure value 0 means that no under pressure is present and increasing values of the pressure 300 on the y-axis is related to increasing under pressure.

Initially, within the first method, a linear pressure 501 ramp is applied on the soft tissue/biological tissue 70 and draws the tissue surface 71 in the area 17 into the aspiration probe cavity 15 until the height h which is equivalent to the position of the bottom opening 144 of the air channel is reached.

This event is detected by a change in slope of the pressure curve 500, shown as pressure curve p1 in FIG. 8. The pressure 301 at this point in time is called closing pressure $p_{close}$, i.e., the pressure which is needed to elevate the tissue 70 until closure of the lower opening of the vertical air tube 143. After reaching this elevation height h, the pressure ramp is increased and ramps up until a certain level of vacuum 303, $p_{max}$, is established in the air channel 41. In the same phase the valve 35 will be opened enabling a progressive equalization of the chamber pressure with atmospheric pressure (similar to the function of the wall opening 16 in FIG. 1). This is illustrated in FIG. 8 as the dotted line for pressure $p_2$. This under pressure will not be measured by the device 110 or device 210 and will not be taken up by the control unit 60, the illustration of $p_2$ is just for explanatory purposes. Device 310 instead, will measure the pressure $p_2$ and it will be taken up by the control unit 60.

When the tissue 70 closes the lower opening 144, then the under pressure in the tube 41 increases rapidly and it is known from previous trials about the necessary time within which the under pressure increases enough to be greater than $p_{open}$, i.e., under pressure at value 302. It is also possible to increase the underpressure in a determined way to said value $p_{max}$, based on a measurement.

After reaching $p_{max}$ at pressure inversion point in time 503 the pressure unit 20 is reversed and a slow increasing pressure ramp 504 is applied in the air channel 41 such that the vacuum level decreases. In simpler embodiments, a valve can be provided in the line of tube 41 which is just opened at that point in time allowing the start of a decrease of the under pressure and no reverse of the pump 20 would be necessary. As soon as the tissue 70 detaches from the vertical air channel end 144 at elevation height h, a change in the slope of $p_1$ can be detected and an increased decrease inverse pressure 505 can be detected. This pressure 302 is called opening pressure $p_{open}$.

When the tissue 70 detaches from the vertical air channel end 144 at elevation height h, the under pressure from the tube is faster reduced by inflowing air from the open valve

35 raising the under pressure according to curve 604 in the cavity 15 until the pressure 604' the tube 41 under pressure is equal to the cavity under pressure and then the under pressure is reduced as in curve portion 604" fast back to the pressure of the ambient room. The time 405 is a characteristic time between the peak 503 and the end of the measurement around curve 604".

Figures 9A, 9B, 9C:
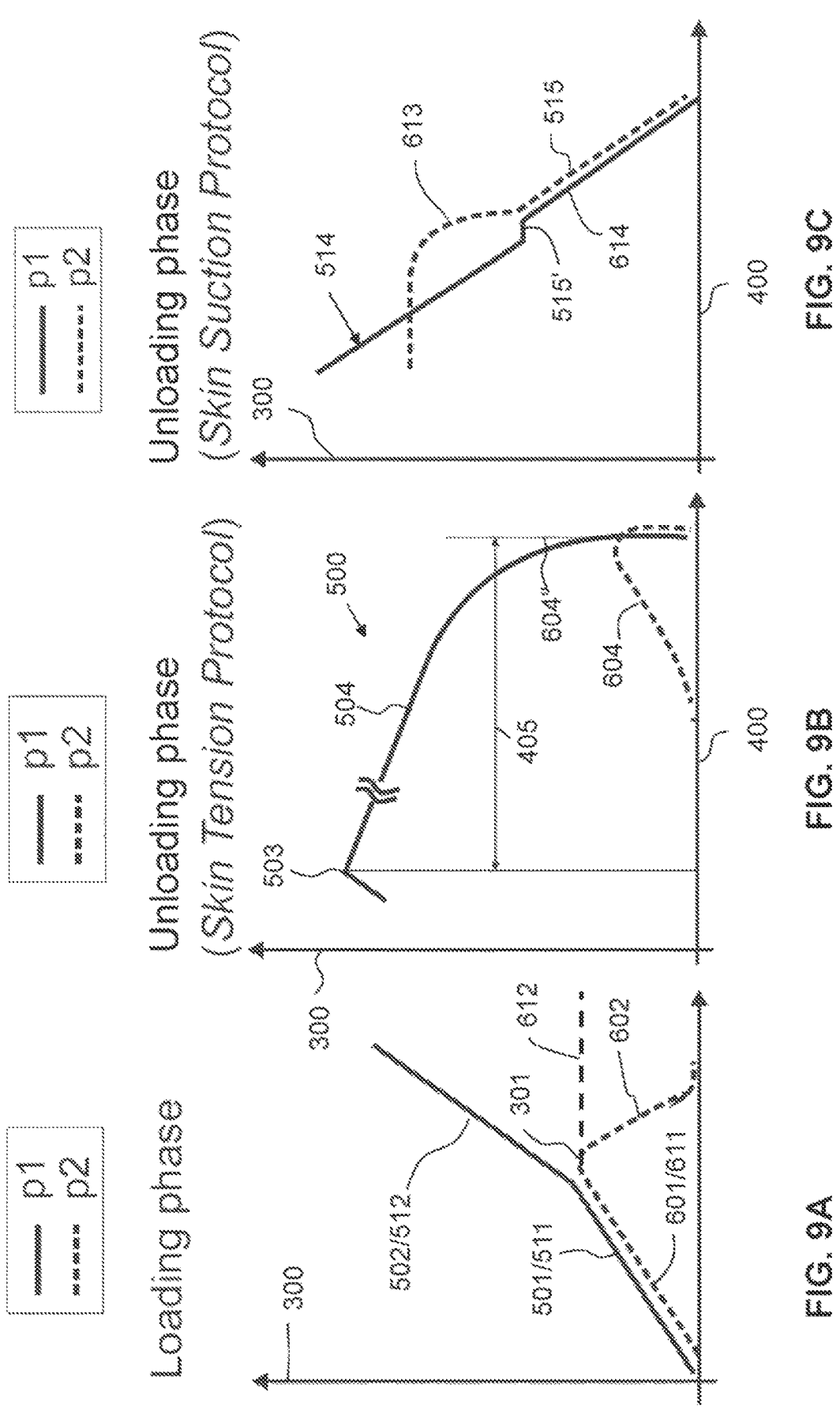
FIG. 9A shows a partial and partially not-to-scale diagram of pressure against time during the loading phase of a measurement cycle of the device according to FIG. 1, 5 or 7, i.e., during the loading phase of all embodiments of the invention.
FIG. 9B shows a partial and partially not-to-scale diagram of pressure against time during the unloading phase of a measurement cycle of the device according to FIG. 1 or one scheme according to FIG. 7, i.e., during the unloading phase of embodiments of the invention applying the tissue tension scheme (not of the device according to FIG. 1, since there is no rise of p2 at the end of the unloading cycles)
FIG. 9C shows a partial and partially not-to-scale diagram of pressure against time during the unloading phase of a measurement cycle of the device according to FIG. 5 or one other protocol according to FIG. 7, i.e., during the unloading phase of embodiments of the invention applying the tissue suction scheme.

FIG. 9A shows a partial and partially not-to-scale diagram of pressure against time during the loading phase of a measurement cycle of the device according to FIG. 1, 5 or 7 for $p_1$, i.e., during the loading phase of all embodiments of the invention, wherein the closing situation of the first air channel 41 is shown in FIG. 9A. It is noted that $p_2$ is shown for the tension scheme and the suction scheme in two different dotted lines. FIG. 9B shows a partial and partially not-to-scale diagram of pressure against time during the unloading phase of a measurement cycle of the device according to the tissue tension scheme as applied in a device according to FIG. 7, i.e., during the unloading phase of embodiments of the invention applying the tissue tension protocol. FIG. 9C shows a partial and partially not-to-scale diagram of pressure against time during the unloading phase of a measurement cycle of the device according to FIG. 5 or the application of the tissue suction scheme according to FIG. 7, i.e., during the unloading phase of embodiments of the invention applying the tissue suction scheme. The reference numerals are identical to the numerals used for the same features in FIGS. 2, 3 and 6.

FIGS. 9A, 9B and 9C show the evaluation methods for the closing and opening pressure in the individual protocols (tissue tension and tissue suction). The closing pressure (for both protocols) corresponds to the maximum chamber pressure p2 in the loading phase. The opening pressure in case of the tissue tension scheme corresponds to the maximum chamber pressure $p_2$ during the unloading phase (note: this is a different pressure value than the $p_{open}$ described in FIG. 2, FIG. 3 and FIG. 8, however, it contains the same time dependent information about the tissue). Additionally, the viscoelastic time parameter 405, $t_{end}$–$t_{max}$, can be extracted. The time parameter 405 defines the time between the start of the tissue retraction (unloading) phase—$t_{max}$—and the end of the measurement—$t_{end}$—where the tissue is completely retracted and the pressure equalized to atmospheric pressure. The opening pressure in case of the tissue suction scheme corresponds to the chamber pressure p2, at the time point when p1 and p2 are equal again for the first time in the unloading phase (|p1–p2|=min). It indicates the time point when the tissue detaches from the vertical air channel, whereby the pressure in the vertical air channel and in the chamber equalize.

Figures 10A, 10B, 10C:
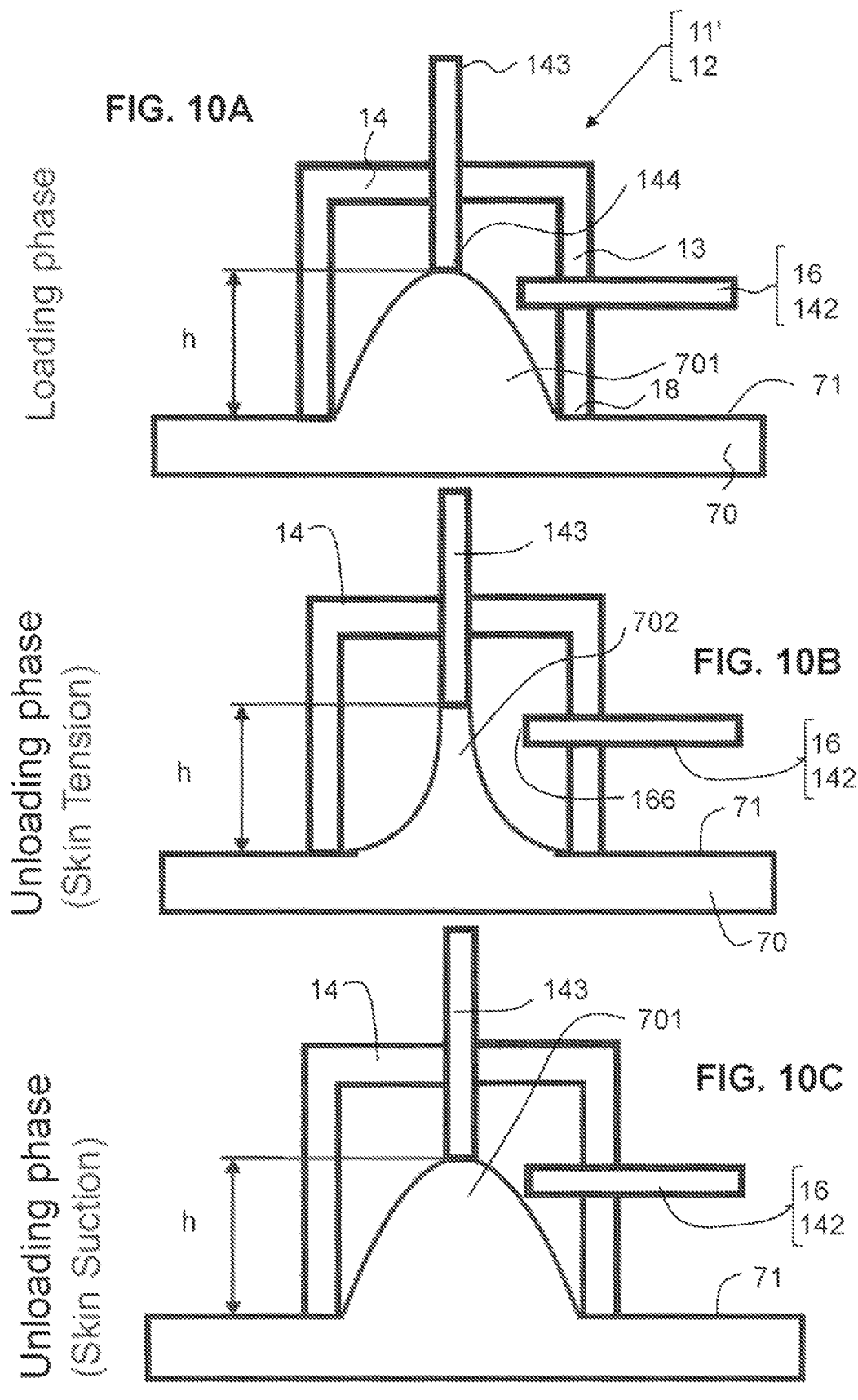
FIG. 10A shows a deformation profile at $p_{close}$ for a tissue sucked in the aspiration device according to FIG. 1, 5 or 7, i.e., during the loading phase of all embodiments of the invention.
FIG. 10B shows a first deformation profile at $p_{open}$ for a tissue sucked in the aspiration device according to FIG. 1 or one other protocol according to FIG. 7 at the beginning of the unloading phase.
FIG. 10C shows a second deformation profile at $p_{open}$ for a tissue sucked in the aspiration device according to FIG. 5 or one other protocol according to FIG. 7 at the end of the unloading phase.

In this method, the tissue deformation profile is dome-like. FIG. 10A also shows the expected tissue deformation during the loading phase when the tissue reaches the elevation height h, at the pressure level $p_{close}$. This behaviour of the sucked in tissue is similar for the first, second and third embodiment during the loading phase, in the first part of the method scheme; therefore FIG. 4A and FIG. 10A are identical, with exception for the opening 16 in the side wall 13 shown in FIG. 4A, which would be replaced by an air channel 142 in FIG. 10A.

FIG. 10B shows the deformation profile at time point $t_{open}$, when the tissue retracts ($p_{open}$) with the tissue tension scheme (e.g., with the device 110 of FIG. 1, i.e., with the open side channel 16; or with the device 310 with the open valve 35). The tissue distribution has a contact surface at the bottom edge 144 of the tube end portion 143 and a change from the dome-like shape during the loading shape towards the mountain-like deformation until the time point when the tissue detaches from the air channel 41 and the pressure p$_{open}$ is extracted.

FIG. 10C shows the deformation profile at time point t$_{open}$, when the tissue retracts (p$_{open}$) with the tissue suction scheme (e.g., with the device 210 of FIG. 5 or device 310 of FIG. 7). Here, the tissue distribution around the bottom edge 144 of the tube end portion 143 is still a dome-like deformation at the time point when the closing pressure p$_{close}$ is evaluated as well as at the time point when the tissue detaches from the air channel 41 and the pressure p$_{open}$ is extracted.

In FIGS. 10A, 10B and 10C the tissue deformation profiles are shown for both protocols. The deformation profile during the loading phase is dome-like for the loading portion of both protocols as shown in FIG. 10A. The tissue is held at the elevation height h, where the closing pressure is extracted (p$_{close}$). For the tissue tension scheme, the deformation profile changes from dome-like to a pointy shape, due to the equalization of the chamber pressure with atmospheric pressure as shown in FIG. 10B. The tissue deformation at the time point of detachment from the vertical air channel, where the opening pressure is extracted (p$_{open}$) is shown. For the tissue suction scheme, the tissue deformation profile is dome-like through the whole course of the measurement as shown in FIG. 10C.

Coming back to the use of the device 210 according to FIG. 5; with this tissue suction scheme a completely different tissue deformation compared to the tissue tension scheme is induced. The outcome of the opening pressure is to be different from p$_{open}$ of the tissue tension scheme as explained above and therefore highlighting other important mechanical properties of the measured tissue. The first part of the measurement, the evaluation of the closing pressure p$_{close}$ is comparable to the one in the tissue tension scheme. Afterwards the load type changes and therefore also the response of the tissue. The opening pressure p$_{open}$ characterizes as well the viscoelastic properties of the tissue, by highlighting the time point when the tissue detaches from the vertical air channel bottom 144. Also, in this protocol, p$_{open}$ depends in the case of a biological tissue to be tested on the microstructure (collagen, fluid flow and proteoglycans) of the investigated tissue.

Further, this method could be used in a cyclic mode to evaluate history dependent tissue effects, i.e., repeating the method steps as reflected by the curve 500 a number of times with same or different time periods in-between.

With this arrangement, three scenarios can be implemented:

A tissue tension scheme with a different approach for measurement, i.e.

a.) Loading phase (until p$_{close}$): valve closed b.) Loading phase (from p$_{close}$ until p$_{max}$): valve open c.) Unloading phase: valve closed.

A tissue suction scheme with two phases:

a.) Loading phase: valve closed b.) Unloading phase: valve closed

A further tissue tension scheme:

a.) Loading phase: valve closed b.) Unloading phase: valve open

However, with this setup the measurement of p$_2$, the chamber pressure, is enabled. Therefore, more information and additional possibilities for evaluation of the closing pressure p$_{close}$ and the opening pressure p$_{open}$ (evaluation with p$_2$) is provided.

For the tissue tension scheme, the valve is closed in the beginning (closed measurement system). An increasing under pressure draws the soft tissue/biological tissue into the aspiration probe cavity 15 until the height h (position of the vertical air channel, the lower open end 144) is reached. This event can either be detected by a change in slope of the pressure curve in the vertical air channel, p$_1$ (solid line) in FIG. 8, or by the first maximum pressure value 301 of the pressure curve in the chamber, p$_2$ (dashed line). It is also called the closing pressure p$_{close}$, the pressure needed to elevate the tissue until closure of the vertical air channel. After reaching the elevation height h, the rate of the increasing under pressure is increased and ramps up until a certain level of vacuum, p$_{max}$, is established in the vertical air channel. During the same phase, the opening of the valve 35 will enable an equalization of the chamber pressure with atmospheric pressure. This is illustrated in FIG. 8 as p$_2$ (dashed line).

After reaching p$_{max}$, the valve 35 is closed again to establish a closed system, the pressure unit 20 is reversed, and an increasing pressure ramp is applied in the vertical air channel such that the vacuum level decreases. As soon as the tissue detaches from the vertical air channel (at elevation height h), a change in the slope of p$_1$ can be detected and indicates an increased air flow from the vertical pressure channel into the chamber. Simultaneously, the chamber pressure p$_2$ will increase and equalize with p$_1$. A second peak in p$_2$ can be determined and indicates the time point when the tissue detaches from the vertical air channel, the opening pressure p$_{open}$.

For the tissue suction scheme, the valve is closed during the whole course of the measurement. An increasing under pressure is applied on the soft tissue/biological tissue and draws it into the aspiration probe cavity 15 until the height h (position of the vertical air channel) is reached. This event can either be detected by a change in slope of the pressure curve p$_1$ (solid line), or by the maximum pressure value of the chamber pressure p$_2$ (dashed line). Shortly after reaching p$_{close}$, the pressure unit 20 is reversed and an increasing pressure ramp is applied. Consequently, the tissue retracts and the pressure at which the tissue detaches from the vertical air channel can be detected (which could give a constant under pressure period at point 515') or by the fact that both pressure curves (p$_1$ and p$_2$) show the identical course again (|p1−p2|=min), in FIG. 9C. This is called the opening pressure p$_{open}$.

Figure 11:
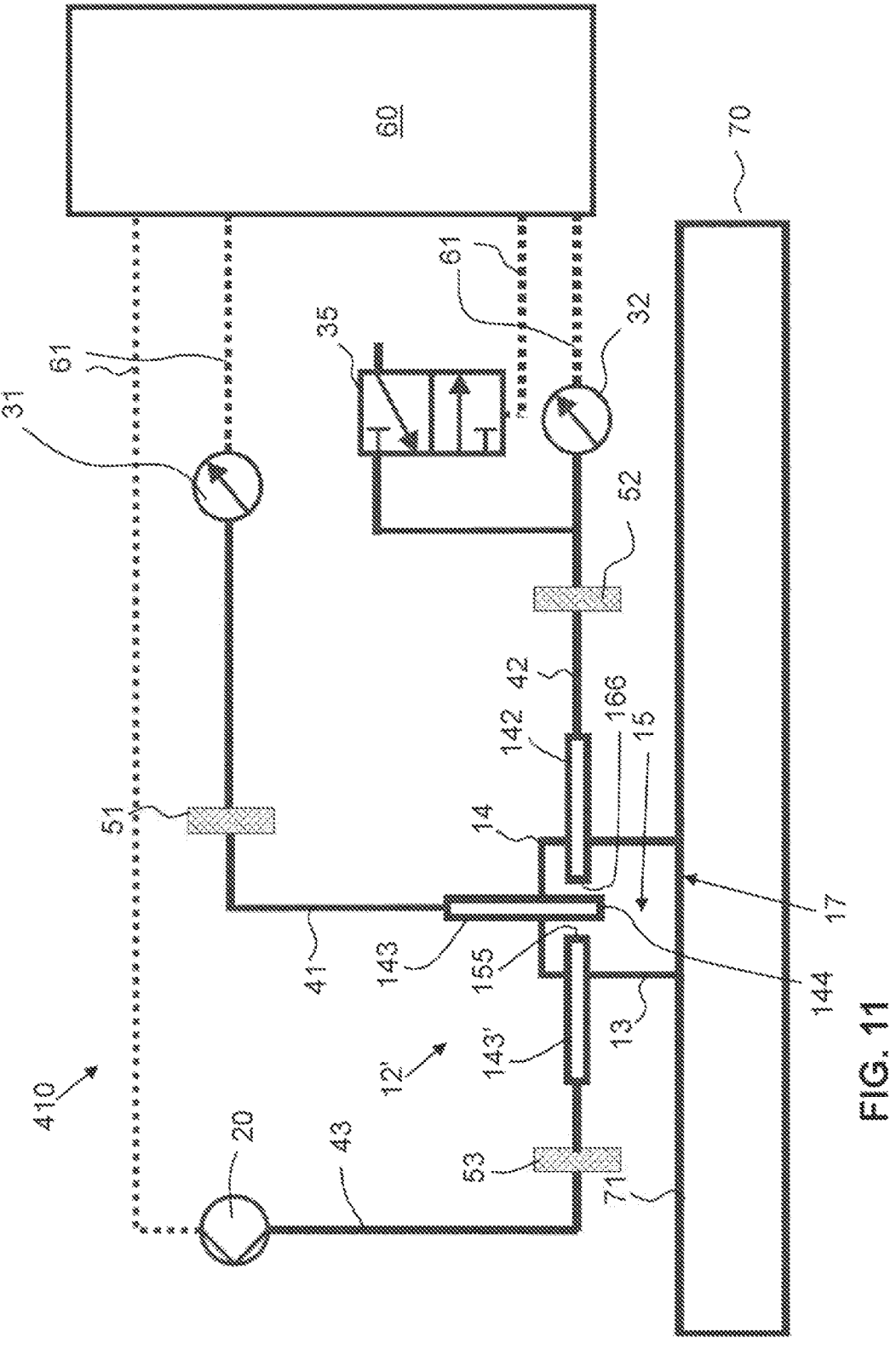
FIG. 11 shows a schematic representation of an aspiration device according to a fourth embodiment of the invention, called a further combined device for providing the application of the tissue tension scheme and the tissue suction scheme with a separated first suction line.

FIG. 11 shows a schematic representation of an aspiration device 410 according to a fourth embodiment of the invention, called a further combined device for providing the application of the tissue tension scheme and the tissue suction scheme with a separated first suction line, separated in an air channel 41 with filter 51 and first pressure sensor 31, while the air is sucked from the probe cavity 15 via a separated suction line 43 with a third air filter 53 in front of the pressure unit 20. Here, the inner opening position 166 providing the possible opening as opening 16 and to attach the second pressure sensor 32, both behind an optional second filter 52 in the second air channel 42 is provided not to interfere with the contact of the tissue with the lower open end 144 of the first pressure sensor 31 for measuring p$_1$. The inner canal opening position 155 is above the lower open end 144 of the first pressure sensor 31. As said for the device according to FIG. 7, the tube end portions 142 and 143' can be oriented in a different way, e.g., in an angle of e.g., 45 degree towards the lower open end 144 through the top wall 14 or just in parallel to the tube end portion 142 with a higher positioned end 155, 166 to allow a sucked in tissue to be pushed against the lower end 144. When the pressure further becomes lower in 15, the pressure will be slightly higher in the air channel 41; since the pressure does not change anymore in the air channel 41. However, this difference is in view of the small volume of channel 41 not enough allowing for the tissue touching at surface 144 to break free from this lower surface 144.

Figure 12:
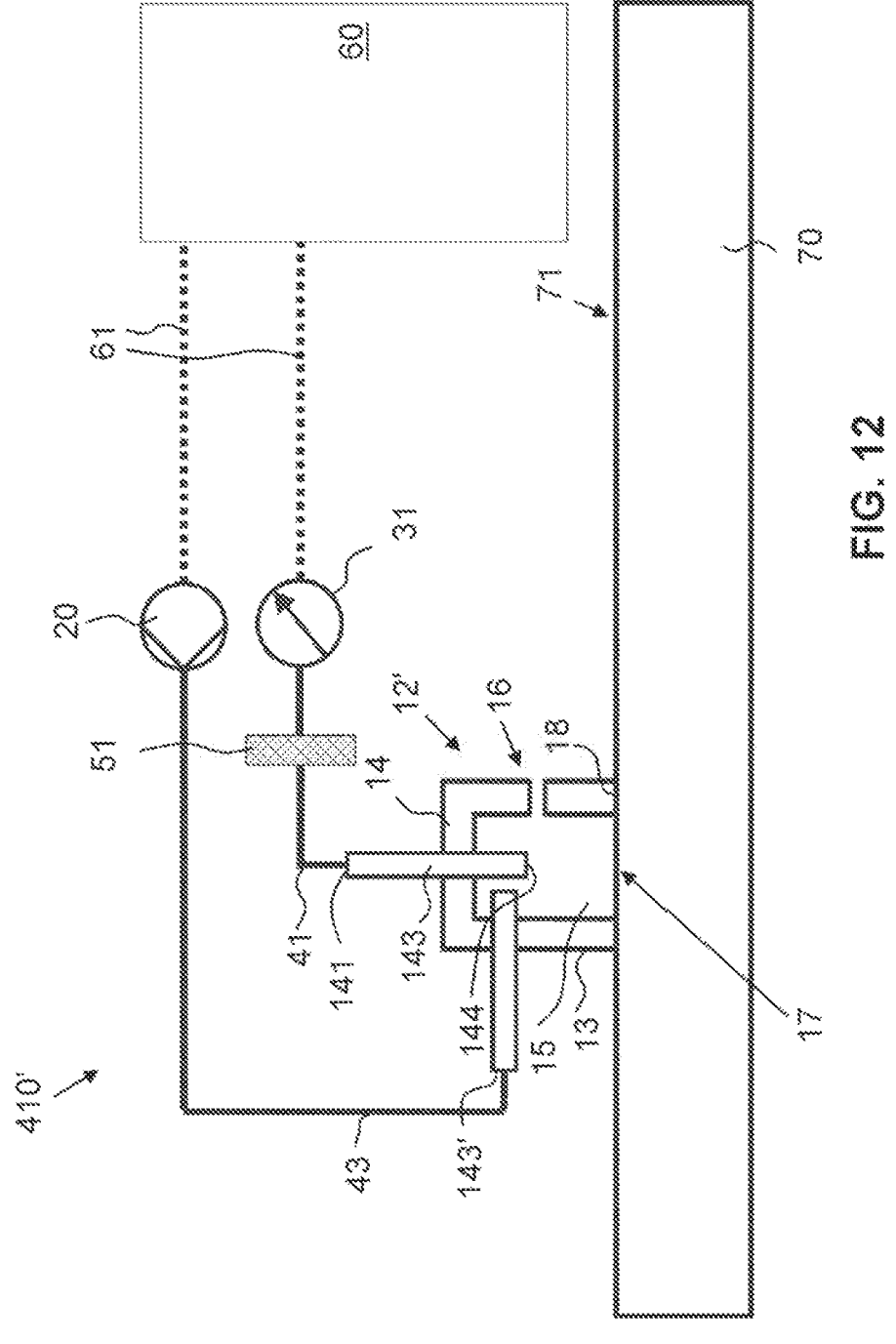
FIG. 12 shows a schematic representation of an aspiration device according to a fifth embodiment of the invention, called a further device for providing the application of the tissue tension scheme with a separated first suction line.

FIG. 12 shows a schematic representation of an aspiration device 410' according to a fifth embodiment of the invention, called a further device for providing the application of the tissue tension scheme with a separated first suction line being a third air channel 43.

With the explained protocols, the tissue stiffness is evaluated in terms of the pressure needed to induce a certain tissue elevation (mbar/mm). This parameter depends on the specific microstructure of the tissue and is mainly determined by the density and configuration of the collagen fibers. The closing pressure $p_{close}$ compared to the elevation height h results in the tissue stiffness:

$$k = \frac{p_{close}}{h}$$

Further, these protocols enable the evaluation of viscoelastic tissue parameters, like the opening pressure ($p_{open}$). After reaching the maximum pressure $p_{max}$, the tissue will experience creep effects. These effects depend strongly on the microstructure, e.g., collagen fibers, the fluid flow within the tissue and the amount of proteoglycans. These phenomena can be characterized with the time parameter $t_{end}-t_{max}$ in the unloading phase of the tissue tension scheme. The pressure at the point of retraction (when the tissue detaches from the vertical air channel), called $p_{open}$, is characteristic for these phenomena. The outcome of the opening pressure $p_{open}$ is different between the tissue tension scheme and the tissue suction scheme and highlighting the difference in mechanical properties of the measured tissue. With these protocols, the tissue release ratio can be evaluated. The release ratio describes the relationship between the opening pressure $p_{open}$ and the closing pressure $p_{close}$:

$$rr = \frac{p_{open}}{p_{close}}$$

Further, the tissue suction scheme can be used in a cyclic mode to evaluate history dependent tissue effects.

| LIST OF REFERENCE SIGNS | |
| --- | --- |
| 11 | aspiration probe |
| 11' | aspiration probe (closed opening) |
| 12 | aspiration probe |
| 12' | aspiration probe (separated suction channel) |
| 13 | side wall |
| 14 | top wall |
| 15 | probe cavity |
| 16 | opening in probe (side) wall |
| 17 | open bottom mouth of cavity |
| 18 | bottom edge |
| 20 | pressure unit |
| 31 | (first) pressure sensor |
| 32 | (second pressure sensor) |
| 35 | valve |
| 41 | (first) air channel (tube) |
| 42 | second air channel (tube) |
| 43 | third air channel (tube) |
| 51 | (first) filter |

-continued

| LIST OF REFERENCE SIGNS | |
| --- | --- |
| 52 | second filter |
| 53 | third filter |
| 60 | control unit |
| 61 | electrical supply and data line |
| 70 | soft tissue (biological tissue) |
| 71 | soft tissue (biological tissue) surface |
| 110 | aspiration device (first embodiment) |
| 141 | adapter |
| 142 | tube end portion |
| 143 | tube end portion |
| 143' | tube end portion |
| 144 | lower open end |
| 155 | inner suction canal opening position |
| 166 | inner opening position |
| 210 | aspiration device (second embodiment) |
| 300 | negative pressure |
| 301 | negative closing pressure |
| 302 | negative opening pressure |
| 303 | maximum negative pressure |
| 310 | aspiration device (third embodiment) |
| 311 | negative closing pressure |
| 312 | negative opening pressure |
| 313 | maximum negative pressure |
| 400 | time |
| 401 | closing time |
| 402 | opening time |
| 405 | characteristic time parameter |
| 410 | aspiration device (fourth embodiment) |
| 410' | aspiration device (fifth embodiment) |
| 411 | closing time |
| 412 | opening time |
| 500 | measured negative pressure curve against time |
| 501 | first linear negative pressure increase |
| 502 | second linear negative pressure increase |
| 503 | inversion point for negative pressure |
| 504 | linear negative pressure decrease |
| 505 | steep negative pressure decrease |
| 506 | crossing point |
| 510 | first measured negative pressure curve against time |
| 511 | first linear negative pressure increase |
| 512 | second linear negative pressure increase |
| 513 | inversion point for negative pressure |
| 514 | first linear negative pressure decrease |
| 515 | second linear negative pressure decrease |
| 515' | intermediate negative pressure increase |
| 600 | negative pressure curve against time in cavity |
| 601 | linear negative pressure increase |
| 602 | hyperbolic negative pressure decrease |
| 603 | minimum negative pressure |
| 604 | hyperbolic negative pressure increase |
| 604' | maximum negative pressure |
| 604" | sharp negative pressure decrease |

15

-continued

LIST OF REFERENCE SIGNS

| | |
|---|---|
| 610 | negative pressure curve against time in cavity |
| 611 | first linear negative pressure increase |
| 612 | maintained constant negative pressure |
| 613 | steep negative pressure decrease |
| 614 | linear negative pressure decrease |

The invention claimed is:

1. An aspiration device for measuring the viscoelastic behaviour of biological tissues and synthetic materials, comprising:

a probe head having the form of a cup with
a cavity,
side wall(s) and
a top wall,
a first probe channel connected to the probe head,
a pressure unit providing a vacuum inside the first probe channel,
a pressure sensor provided in the first probe channel for detecting the pressure in the first probe channel, and
a control unit connected to the pressure unit for controlling the pressure unit,
wherein the first probe channel has a distal end leading with its lower open end through the top wall into the cavity of the probe head,
wherein the cavity comprises an opening in the side or in the top wall,
wherein the control unit is configured to execute a measurement cycle comprising applying under pressure in the first probe channel, measuring the under pressure with the pressure sensor, detecting a change of under pressure increase over time, increasing the under pressure to a predetermined maximum under pressure, decreasing the under pressure beyond this point in time and detecting a change of under pressure decrease over time, and
wherein the control unit is configured to calculate from the pressure values received and time values measured output values from the group comprising the closing pressure value $p_{close}$ and closing time value $t_{close}$ at the change of under pressure increase over time, the opening pressure value $p_{open}$ and opening time value $t_{open}$ at the change of under pressure decrease over time as well as the tissue stiffness and the release ratio $$rr = \frac{p_{open}}{p_{close}}.$$

2. The aspiration device according to claim 1, wherein the lower open end is extending into the cavity.

3. The aspiration device according to claim 1, wherein the cavity comprises an opening in the side or in the top wall.

4. The aspiration device according to claim 1, wherein a filter is provided in the first probe channels.

5. An aspiration device for measuring the viscoelastic behaviour of biological tissues and synthetic materials, comprising:

a probe head having the form of a cup with
a cavity,

16 side wall(s) and
a top wall,
a first probe channel connected to the probe head,
a second probe channel connected to the probe head,
a pressure unit providing a vacuum inside the first probe channel,
a pressure sensor provided in the first probe channel for detecting the pressure in the first probe channel,
a valve closing the second probe channel, and
a control unit connected to the pressure unit for controlling the pressure unit and connected to the valve for controlling the valve,
wherein the first probe channel has a distal end leading with its lower open end through the top wall into the cavity of the probe head,
wherein the control unit is configured to execute a measurement cycle comprising applying under pressure in the first probe channel, measuring the under pressure with the pressure sensor, detecting a change of under pressure increase over time, increasing the under pressure to a predetermined maximum under pressure, decreasing the under pressure beyond this point in time and detecting a change of under pressure decrease over time, and
wherein the control unit is configured to calculate from the pressure values received and time values measured output values from the group comprising the closing pressure value $p_{close}$ and closing time value $t_{close}$ at the change of under pressure increase over time, the opening pressure value $p_{open}$ and opening time value $t_{open}$ at the change of under pressure decrease over time as well as the tissue stiffness and the release ratio $$rr = \frac{p_{open}}{p_{close}}.$$

6. The aspiration device according to claim 5, the control unit is configured to execute the measurement cycle while the valve is open over the measurement cycle.

7. The aspiration device according to claim 5, the control unit is configured to execute the measurement cycle while the valve is closed over the measurement cycle.

8. The aspiration device according to claim 5, wherein a filter is provided in at least one of the first and second probe channels.

9. An aspiration device for measuring the viscoelastic behaviour of biological tissues and synthetic materials, comprising:

a probe head having the form of a cup with
a cavity,
side wall(s) and
a top wall,
a first probe channel connected to the probe head and having a first open end,
a third probe channel connected to the probe head and having a third open end,
a pressure unit providing a vacuum inside the third probe channel,
a pressure sensor provided in the first probe channel for detecting the pressure in the first probe channel,
a control unit connected to the pressure unit for controlling the pressure unit,
wherein the first probe channel has a distal end leading with its first open end through the top wall into the cavity of the probe head,

wherein the third open end is positioned nearer to the top wall than the first open end, wherein the control unit is configured to execute a measurement cycle comprising applying under pressure in the third probe channel, measuring the under pressure with the pressure sensor, detecting a change of under pressure increase over time, increasing the under pressure to a predetermined maximum under pressure, decreasing the under pressure beyond this point in time and detecting a change of under pressure decrease over time, and wherein the control unit is configured to calculate from the pressure values received and time values measured output values from the group comprising the closing pressure value $p_{close}$ and closing time value $t_{close}$ at the change of under pressure increase over time, the opening pressure value $p_{open}$ and opening time value $t_{open}$ at the change of under pressure decrease over time as well as the tissue stiffness and the release ratio $$rr = \frac{p_{open}}{p_{close}}.$$

10. The aspiration device according to claim 9, further comprising:

a second probe channel connected to the probe head and having a second open end, and a valve closing the second probe channel, wherein the control unit is connected to the valve for controlling the valve, and wherein the second open end is positioned nearer to the top wall than the first open end.

11. A method for measuring the viscoelastic deformability of biological tissues and synthetic materials from the group encompassing tissues to be tested in-vivo: skin and mucous membranes of humans or animals, especially directly reachable surfaces inside the mouth, nose, vagina, cervix; tissues and materials to be tested ex-vivo and in-vitro: compliant elastomers or other synthetic materials, hydrogels, tissue engineering scaffolds, decellularized extracellular matrix, cellulose based materials, organotypic in-vitro systems, or soft implants, especially breast implant bodies or meshes with closed mainly impermeable surfaces, as well as tissues and tissue materials and materials to be tested in-vivo and ex-vivo: artificial skin or skin substitute by making available an aspiration apparatus having a probe head having the form of a cup with a cavity, one or more side walls and a top wall, a first probe channel connected to the probe head, a pressure unit providing a vacuum inside the first probe channel, a pressure sensor provided in the first probe channel for detecting the pressure in the first probe channel, and a control unit connected to the pressure unit for controlling the pressure unit, wherein the first probe channel has a distal end leading with its lower open end through the top wall into the cavity of the probe head and wherein the cavity comprises an opening in the side or in the top wall, contacting the probe head with the biological tissue or synthetic material,

applying an under pressure on the biological tissue or material via the first probe channel in the cavity, increasing, in the cavity, the under pressure to a predetermined maximum under pressure, decreasing the under pressure beyond the point in time when the predetermined maximum under pressure is reached, and detecting a change of under pressure decrease over time, determining by the control unit at least one output value from the group comprising the closing pressure value $p_{close}$ when the biological tissue or synthetic material closes the first probe channel during under pressure increase, the closing time value $t_{close}$ when the biological tissue or synthetic material closes the first probe channel during under pressure increase, the opening pressure value $p_{open}$ when the biological tissue or synthetic material re-opens the first probe channel during under pressure decrease, the opening time value $t_{open}$ when the biological tissue or synthetic material re-opens the first probe channel during under pressure decrease, wherein one or both of the closing pressure value $p_{close}$ and the closing time value $t_{close}$ are determined based on the different slope of the under pressure increase when the biological tissue or synthetic material closes the first probe channel during under pressure increase.

12. The method according to claim 11, wherein one or both of the opening pressure value $p_{open}$ and the opening time value $t_{open}$ is determined based on the detection of a pressure drop above a threshold value, especially a pressure drop above a threshold value to atmospheric pressure during the under pressure decrease when the cavity has a side opening or comprises an open valve, when the biological tissue or synthetic material re-opens the first probe channel during under pressure decrease.

13. The method according to claim 11, wherein one or both of the opening pressure value $p_{open}$ and the opening time value $t_{open}$ are determined based on the detection of a constant under pressure time during the under pressure decrease when the cavity is closed beside the first probe channel or comprises a closed valve, when the biological tissue or synthetic material re-opens the first probe channel during under pressure decrease.

14. The method according to claim 11, wherein, in the determination step, the control unit is configured to calculate the tissue stiffness k as $$k = \frac{p_{close}}{h},$$

wherein the height h is the distance between the bottom edge of the probe head and the lower open end of the first probe channel ending in the probe head.

15. The method according to claim 11, wherein the control unit is configured to calculate the release ratio rr as $$rr = \frac{p_{open}}{p_{close}}.$$

* * * * *